(12) United States Patent
Tokida

(10) Patent No.: US 11,116,477 B2
(45) Date of Patent: Sep. 14, 2021

(54) IMAGING PROBE FOR DIAGNOSIS

(71) Applicant: TERUMO KABUSHIKI KAISHA, Tokyo (JP)

(72) Inventor: Masanori Tokida, Fujinomiya (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 639 days.

(21) Appl. No.: 15/460,480

(22) Filed: Mar. 16, 2017

(65) Prior Publication Data
US 2017/0181728 A1 Jun. 29, 2017

Related U.S. Application Data

(63) Continuation of application No. PCT/JP2015/077171, filed on Sep. 25, 2015.

(30) Foreign Application Priority Data

Sep. 26, 2014 (JP) .............................. JP2014-197499

(51) Int. Cl.
*A61B 8/00* (2006.01)
*A61B 8/12* (2006.01)
(Continued)

(52) U.S. Cl.
CPC .............. *A61B 8/4416* (2013.01); *A61B 1/07* (2013.01); *A61B 5/0035* (2013.01);
(Continued)

(58) Field of Classification Search
CPC ........... A61B 8/00; A61B 8/12; A61B 8/0891; A61B 8/5261; A61B 8/5223; A61B 8/445;
(Continued)

(56) References Cited

U.S. PATENT DOCUMENTS 8,214,010 B2* 7/2012 Courtney ............. A61B 5/0095
600/407
8,356,517 B2* 1/2013 Buccafusca ............. G01H 9/00
73/601
(Continued)

FOREIGN PATENT DOCUMENTS

JP 11-056752 A 3/1999
JP 2002-153472 A 5/2002
(Continued)

OTHER PUBLICATIONS

WO2013145689A1—translation (Year: 2013).*
(Continued)

*Primary Examiner* — Oommen Jacob
(74) *Attorney, Agent, or Firm* — Buchanan Ingersoll & Rooney PC

(57) ABSTRACT

An imaging probe is disclosed for diagnosis, which includes an imaging core having a drive shaft internally provided with an optical fiber and a signal line. The imaging probe for diagnosis includes an optical transceiver that is disposed in one end of the optical fiber, and an ultrasound transceiver that is joined to the signal line. The optical transceiver is arranged on a distal side of the imaging core from the ultrasound transceiver. An emitting direction of an ultrasound wave emitted from the ultrasound transceiver and an emitting direction of light emitted from the optical transceiver are substantially parallel to each other, and are directions, which further tilt to a proximal end of the drive shaft than a direction orthogonal to the drive shaft.

16 Claims, 5 Drawing Sheets

(51) Int. Cl.
*A61B 8/08* (2006.01)
*A61B 1/07* (2006.01)
*A61B 5/00* (2006.01)
*A61B 5/02* (2006.01)

(52) U.S. Cl.
CPC .......... *A61B 5/0066* (2013.01); *A61B 5/0084* (2013.01); *A61B 5/02007* (2013.01); *A61B 5/7282* (2013.01); *A61B 8/0891* (2013.01); *A61B 8/12* (2013.01); *A61B 8/445* (2013.01); *A61B 8/5223* (2013.01); *A61B 8/5261* (2013.01); *A61B 2562/0233* (2013.01); *A61B 2562/06* (2013.01)

(58) Field of Classification Search
CPC ............. A61B 8/4416; A61B 5/02007; A61B 5/0084; A61B 5/0066; A61B 5/0035; A61B 1/07; A61B 5/7282; A61B 2562/0233; A61B 2562/06; A61B 8/08; A61B 8/485; A61B 5/05; A61B 8/4461; A61B 5/055; A61B 5/6852; A61B 5/0073; A61B 8/0833; G01J 3/02; G01J 3/0202; G01J 3/021; G01J 3/0218; G01J 3/024; G01J 3/0264; G01J 3/0286; G01J 3/0289; G01J 3/10
USPC .................................. 600/407, 427, 459, 478
See application file for complete search history.

(56) References Cited

U.S. PATENT DOCUMENTS

| | | | | |
|---|---|---|---|---|
| 8,753,281 B2 * | 6/2014 | Schmitt | ................ | A61B 5/0095 600/467 |
| 8,784,321 B2 * | 7/2014 | Courtney | ........... | A61B 1/00172 600/463 |
| 8,926,519 B2 * | 1/2015 | Vardi | ..................... | G01H 9/004 600/463 |
| 10,076,248 B2 * | 9/2018 | Rozental | ............ | A61B 1/00071 |
| 10,105,062 B2 * | 10/2018 | Wang | .................... | A61B 5/0062 |
| 2006/0184042 A1 * | 8/2006 | Wang | ................... | A61B 5/0095 600/476 |
| 2007/0038110 A1 * | 2/2007 | Flesch | .................. | A61B 8/4461 600/459 |
| 2009/0043191 A1 * | 2/2009 | Castella | ............... | A61B 5/0066 600/425 |
| 2009/0203991 A1 * | 8/2009 | Papaioannou | ....... | A61B 5/0066 600/421 |
| 2009/0253989 A1 | 10/2009 | Caplan et al. | | |
| 2009/0281430 A1 | 11/2009 | Wilder | | |
| 2011/0098572 A1 * | 4/2011 | Chen | .................... | A61B 5/0066 600/463 |
| 2012/0172698 A1 * | 7/2012 | Teo | ...................... | A61B 5/6852 600/407 |
| 2012/0271170 A1 * | 10/2012 | Emelianov | ........... | A61B 8/0891 600/439 |
| 2013/0012811 A1 * | 1/2013 | Schmitt | ................ | A61B 5/0066 600/427 |
| 2013/0303907 A1 * | 11/2013 | Corl | ....................... | A61B 8/445 600/441 |
| 2014/0142432 A1 * | 5/2014 | Hutchins | .............. | A61B 5/0035 600/462 |
| 2015/0005626 A1 | 1/2015 | Kaneko | | |
| 2015/0351722 A1 * | 12/2015 | Chen | ..................... | A61B 8/445 600/427 |
| 2017/0181728 A1 * | 6/2017 | Tokida | ..................... | A61B 8/12 |

FOREIGN PATENT DOCUMENTS

| | | |
|---|---|---|
| JP | 2003-325526 A | 11/2003 |
| JP | 2011-516865 A | 5/2011 |
| WO | WO 2013/145689 A1 | 10/2013 |
| WO | WO-2013145689 A1 * | 10/2013 |

OTHER PUBLICATIONS

International Search Report (PCT/ISA/210) dated Dec. 8, 2015, by the Japanese Patent Office as the International Searching Authority for International Application No. PCT/JP2015/077171.

Written Opinion (PCT/ISA/237) dated Dec. 8, 2015, by the Japanese Patent Office as the International Searching Authority for International Application No. PCT/JP2015/077171.

Extended European Search Report dated Jun. 4, 2018 issued in corresponding European Patent Application No. 15844199.8.

* cited by examiner

IMAGING PROBE FOR DIAGNOSIS

CROSS-REFERENCES TO RELATED APPLICATIONS

This application is a continuation of International Application No. PCT/JP2015/077171 filed on Sep. 25, 2015, which claims priority to Japanese Application No. 2014-197499 filed on Sep. 26, 2014, the entire contents of which are incorporated herein by reference.

TECHNICAL FIELD

The present disclosure relates to an imaging probe for diagnosis used for diagnosing a biological lumen such as blood vessels.

BACKGROUND DISCUSSION

When a stenotic lesion appearing inside a biological lumen such as blood vessels and vascular channels is percutaneously treated, in order to observe a nature of the lesion or to observe a post-treatment condition, a catheter for diagnosis is used which acquires a tomographic image inside the biological lumen by using an ultrasound wave or light.

In intravascular ultrasound (IVUS) diagnosis, a rotatable imaging core having an ultrasound transducer is disposed in a distal end of an insertion unit. Rotary scanning (radial scanning) is generally performed via a drive shaft extending from the imaging core to a user's hand-side drive unit.

In addition, in optical coherence tomography (OCT) utilizing wavelength sweeping, an imaging core having an optical transceiver attached to a distal end of an optical fiber is present, and is rotated via a drive shaft extending from the imaging core to a user's hand-side drive unit. While the imaging core is rotated, near-infrared light is emitted to a vascular lumen from the optical transceiver in the distal end, and reflected light is received from a biological tissue. In this manner, the radial scanning is performed inside the blood vessel. Then, based on interference light generated by interference between the received reflected light and reference light, a cross-sectional image of the blood vessel is generally visualized.

Although OCT can obtain a high resolution image, OCT can obtain only an image captured from a vascular lumen surface to a relatively shallow tissue. On the other hand, in a case of IVUS, whereas the obtainable image resolution is lower than that of OCT, IVUS can obtain an image of vascular tissue, which is deeper than that in OCT. Therefore, there has been proposed an imaging apparatus for diagnosis (imaging apparatus for diagnosis which includes an ultrasound transceiver capable of transmitting and receiving an ultrasound wave and an optical transceiver capable of transmitting and receiving light) that has an imaging core in which an IVUS function and an OCT function are combined with each other (refer to JP-A-11-56752).

However, according to a dual sensor disclosed in JP-A-11-56752, a lens for OCT is arranged at a position close to a drive shaft, and an ultrasound transducer for IVUS is arranged at a position far from the drive shaft. Here, when an imaging core is manufactured, an end portion of the ultrasound transducer and a conductive wire extending from the drive shaft side are joined (soldered) to each other. Therefore, solder (joining material) is scattered during soldering, thereby causing a possibility that the solder may adhere to the lens located close to the end portion of the ultrasound transducer. In addition, the lens is likely to receive thermal influences from the solder or iron during the soldering. Furthermore, considering the scattering solder, the thermal influence during the soldering, or a wiring space, a mountable lens size has a strictly fixed upper limit.

SUMMARY

The present disclosure is made in view of the above-described problem, and provides a technique for minimizing possibilities that lens performance may be adversely affected by a scattered joining material or heat generated during joining of the end portion of the ultrasound transducer and the conductive wire extending from the drive shaft side.

An imaging probe is disclosed for diagnosis, which includes an imaging core having a drive shaft internally provided with an optical fiber and a signal line. The imaging probe for diagnosis includes an optical transceiver that is disposed in one end of the optical fiber, and an ultrasound transceiver that is joined to the signal line. The optical transceiver is arranged on a distal side of the imaging core from the ultrasound transceiver. An emitting direction of an ultrasound wave emitted from the ultrasound transceiver and an emitting direction of light emitted from the optical transceiver are substantially parallel to each other, and are directions, which further tilt to a proximal end of the drive shaft than a direction orthogonal to the drive shaft.

According to the present invention, it is possible to minimize possibilities that lens performance may be affected by a scattered joining material or heat generated during joining.

Other features and advantageous effects according to the present invention will become apparent from the following description made with reference to the accompanying drawings. Note that in the accompanying drawings, the same reference numerals will be given to the same or similar configurations.

BRIEF DESCRIPTION OF THE DRAWINGS

The accompanying drawings are incorporated in the description, configure a part of the description, illustrate embodiments of the present disclosure and are used to explain principles of the present disclosure as well as describes the embodiments.

DETAILED DESCRIPTION

Figure 1:
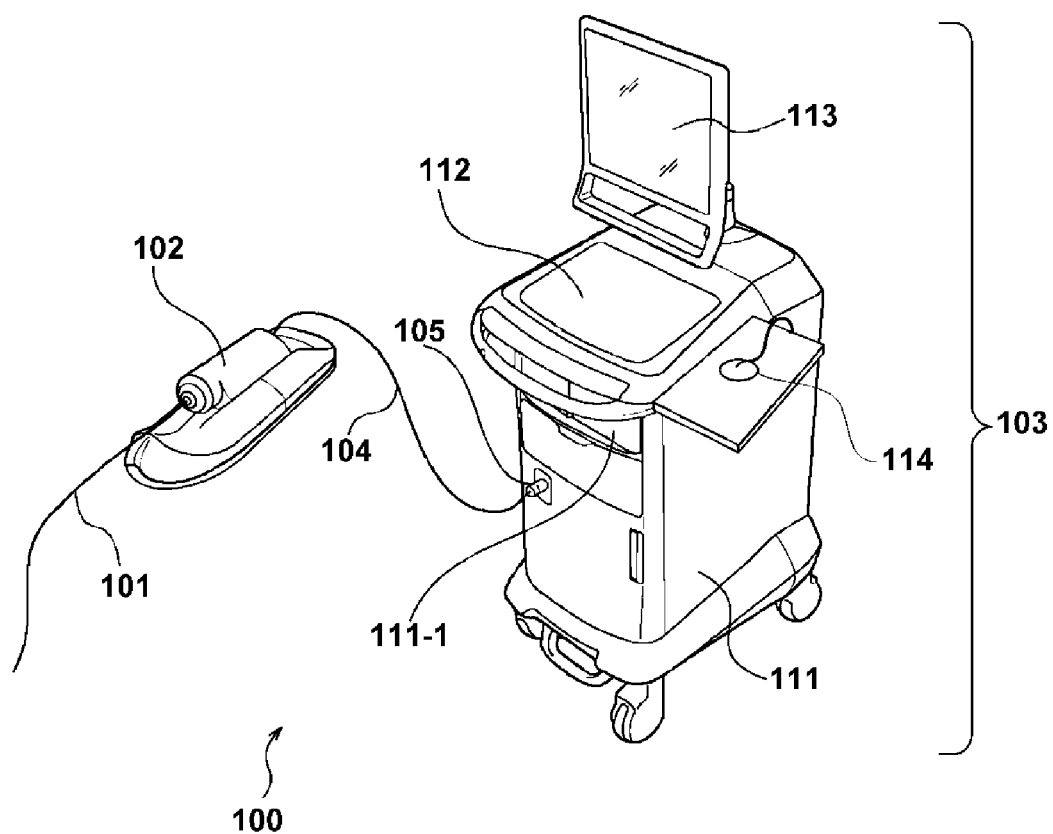
FIG. 1 is a view illustrating an external configuration of an imaging apparatus for diagnosis according to an embodiment of the present disclosure.

Hereinafter, each embodiment according to the present disclosure will be described in detail with reference to the accompanying drawings. Note that since embodiments described below are preferred embodiments of the present disclosure, there are various limitations, which are technically preferable. However, in the following description, unless otherwise described to limit the present disclosure, the scope of the present disclosure is not limited to these embodiments. In addition, throughout the description, the same reference numerals represent the same configuration elements.

FIG. 1 is a view illustrating an external configuration of an imaging apparatus for diagnosis 100 according to an embodiment of the present disclosure. The imaging apparatus for diagnosis 100 according to the present embodiment has an IVUS function and an OCT function.

As illustrated in FIG. 1, the imaging apparatus for diagnosis 100 can include an imaging probe for diagnosis 101, a scanner and pull-back unit 102, and an operation control device 103. The scanner and pull-back unit 102 and the operation control device 103 are connected to each other via a connector 105 by a cable 104, which accommodates a signal line and an optical fiber.

The imaging probe for diagnosis 101 is directly inserted into a blood vessel. A catheter, which accommodates an imaging core, is inserted into the imaging probe for diagnosis 101. The imaging core can include an ultrasound transceiver which transmits an ultrasound wave based on a pulse signal and which receives a reflected wave from the inside of the blood vessel, and an optical transceiver which continuously transmits transmitted light (measurement light) to the inside of the blood vessel and which continuously receives reflected light from the inside of the blood vessel. The imaging apparatus for diagnosis 100 measures a state inside the blood vessel by using the imaging core.

The imaging probe for diagnosis 101 is detachably attached to the scanner and pull-back unit 102, and the scanner and pull-back unit 102 drives an embedded motor, thereby regulating motion, in an axial direction of the blood vessel, and rotation motion of the imaging core in the imaging probe for diagnosis 101 inserted into a catheter sheath. In addition, the scanner and pull-back unit 102 acquires a signal of the reflected wave received by the ultrasound transceiver inside the imaging core and the reflected light received by the optical transceiver, and transmits both of these to the operation control device 103.

In order to perform measurement, the operation control device 103 is provided with a function for inputting various setting values and a function for displaying various blood vessel images after processing ultrasound wave data or optical interference data obtained by measurement.

In the operation control device 103, the reference numeral 111 represents a main body control unit. The main body control unit 111 generates line data from the signal of the reflected ultrasound wave obtained by the measurement, and generates an ultrasound wave tomographic image through interpolation processing.

Furthermore, the main body control unit 111 generates interference light data by causing the reflected light from the imaging core to interfere with reference light obtained by separating light from a light source. Based on the interference light data, the main body control unit 111 generates the line data, and generates a blood vessel tomographic image based on light interference through the interpolation processing.

The reference numeral 111-1 represents a printer & DVD recorder, which prints a processing result in the main body control unit 111 or stores the processing result as data. The reference numeral 112 represents an operation panel. A user inputs various setting values and instructions via the operation panel 112. The reference numeral 113 represents an LCD monitor serving as a display apparatus. The LCD monitor 113 displays various tomographic images generated by the main body control unit 111. The reference numeral 114 represents a mouse serving as a pointing device (coordinate input device).

Figure 2:
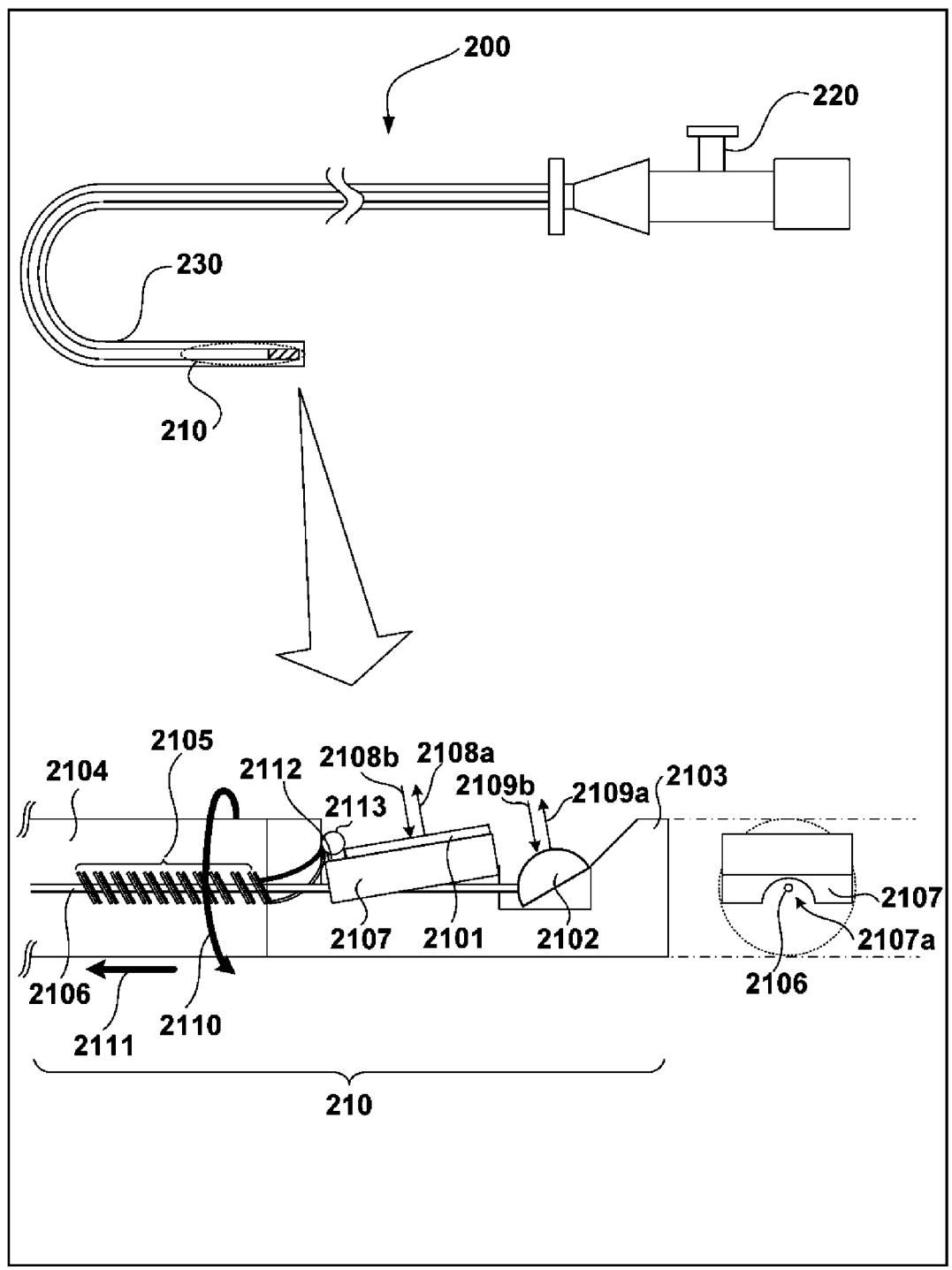
FIG. 2 is a view illustrating a structure example of an imaging core and a catheter accommodating the imaging core according to an embodiment of the present disclosure.

Next, referring to FIG. 2, a structure of an imaging core 210 and a structure of a catheter 200 accommodating the imaging core 210 will be described. The reference numeral 200 in FIG. 2 represents a catheter according to the present embodiment. In addition, the catheter 200 corresponds to the imaging probe for diagnosis 101 in FIG. 1. An injection port 220 for injecting a transparent liquid (for example, physiological salt solution) into a catheter sheath 230 is disposed in the vicinity of a rear end (end portion connected to the pullback unit 102) in the catheter 200.

In addition, the catheter sheath 230 of the catheter 200 is configured to include a transparent material, and internally accommodates the imaging core 210, which is rotatable and movable along the catheter 200. The imaging core 210 can include a drive shaft 2104, and a housing 2103 is disposed in one end of the drive shaft 2104. The housing 2103 accommodates an ultrasound transceiver 2101 and an optical transceiver 2102. The ultrasound transceiver 2101 is supported by a backing member 2107. In addition, the housing 2103 is supported by the drive shaft 2104.

The drive shaft 2104 is configured to include a flexible material which has a characteristic capable of excellently transmitting rotation, for example, a multiplex-multilayer contact coil made of a metal wire such as stainless steel. Then, the drive shaft 2104 internally accommodates a signal line 2105 and an optical fiber 2106. An end portion of the signal line 2105 is joined to an electrode 2112 of the ultrasound transceiver 2101 on the backing member 2107 by soldering (solder 2113). Here, since the backing member 2107 is provided, reflection from a rear surface side of the ultrasound transceiver 2101 can be restrained, and reflection from a side other than a vascular lumen surface can be restrained.

The electrode 2112 is connected to an ultrasound transducer, which configures the ultrasound transceiver 2101. The signal line 2105 and the electrode 2112 of the ultrasound transceiver 2101 are joined to each other in one end on a side far from the optical transceiver 2102, which is one end of the ultrasound transceiver 2101. The backing member 2107 has a groove portion 2107a for allowing the optical fiber 2106 to pass therethrough. In this manner, a diameter of the imaging core 210 can be formed relatively small.

In addition, the housing 2103 is a cylindrical metal pipe, and partially has a cutout portion. The ultrasound transceiver 2101 and the optical transceiver 2102 transmit and receive an ultrasound wave and light via the cutout portion.

The ultrasound transceiver 2101 emits the ultrasound wave toward an illustrated arrow 2108a in accordance with a pulse signal applied from the signal line 2105, detects the reflected wave from a vascular tissue illustrated by an arrow 2108b, and transmits the reflected wave to the signal line 2105 after converting the reflected wave into an electric signal.

The optical transceiver 2102 is disposed in an end portion of the optical fiber 2106, and has a hemispherical shape in which a spherical body is cut at an angle of approximately 45 degrees from a vertical plane in the drawing. A mirror portion is formed on a slope of the optical transceiver 2102. In addition, the optical transceiver 2102 has the hemispherical shape. In this manner, a lens function is also provided therefor. The light supplied via the optical fiber 2106 is reflected on the mirror portion, and is emitted toward the vascular tissue along an illustrated arrow 2109a. Then, the optical transceiver 2102 receives the reflected light from the vascular tissue indicated by an illustrated arrow 2109b. The reflected light is reflected on the mirror portion, and returns to the optical fiber 2106.

When scanning is performed, in accordance with driving of a radial scanning motor of the pullback unit 102, the drive shaft 2104 is rotated along an arrow 2110, and is moved along an arrow 2111. As a result, while the ultrasound transceiver 2101 and the optical transceiver 2102, which are accommodated in the housing 2103 are rotated and moved in the axial direction, both of these respectively emit the ultrasound wave and detect the reflected wave, and emit the light and detect the reflected light.

Figure 3:
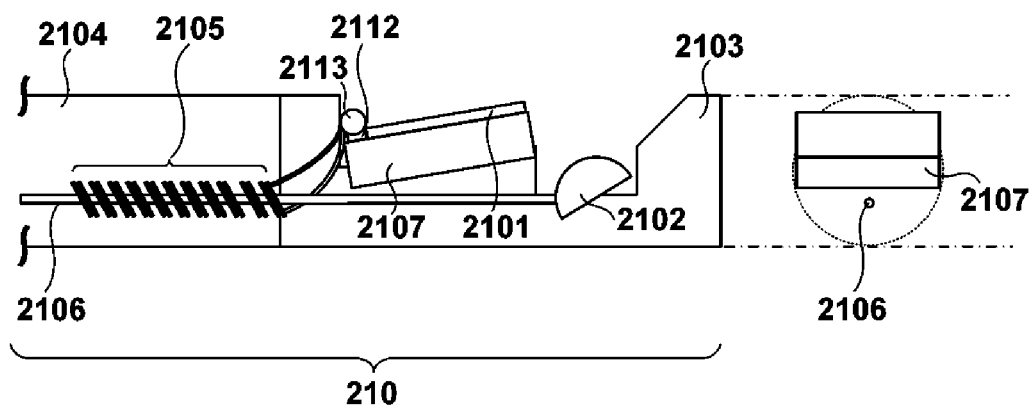
FIG. 3 is a view illustrating a modification example of the structure of the imaging core according to the embodiment of the present disclosure.

Note that in the example illustrated in FIG. 2, the groove portion 2107a for allowing the optical fiber 2106 to pass therethrough is formed in the backing member 2107. However, as illustrated in FIG. 3, a central axis of the optical fiber 2106 may be eccentric from a central axis of the drive shaft 2104. In this manner, a configuration may be adopted in which the optical fiber 2106 is arranged along the backing member 2107 without coming into contact with the backing member 2107.

As illustrated in FIGS. 2 and 3, according to the present embodiment, the ultrasound transceiver 2101 is arranged on the drive shaft 2104 side, and the optical transceiver 2102 is arranged on the distal portion side. In this manner, compared to a case where both of these are conversely arranged, the electrode 2112 and the optical transceiver 2102 can be separated farther from each other. Therefore, it is possible to minimize possibilities that lens performance of the optical transceiver 2102 may be affected by scattered solder during manufacturing or heat generated during soldering. In addition, the signal line 2105 does not extend to a space of the cutout portion. Accordingly, the space can be effectively utilized, and the optical transceiver 2102 can be configured to have a larger lens size.

Figure 4:
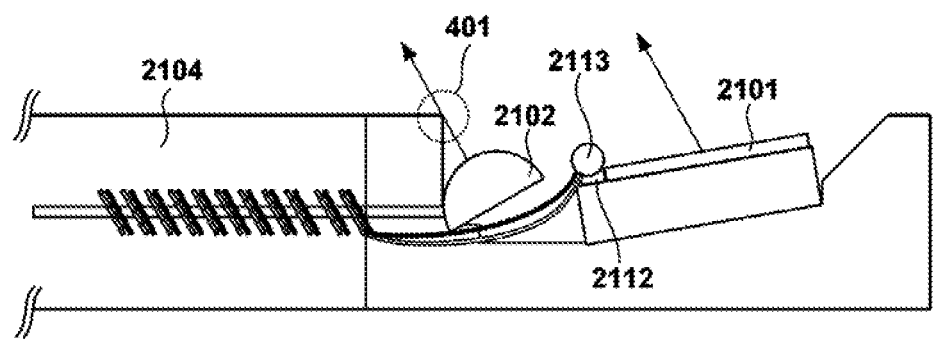
FIG. 4 is a view for describing a problem in a case where an ultrasound transceiver is arranged on a distal portion side of a catheter and an optical transceiver is arranged on a drive shaft side in the related art, compared to the present disclosure.

FIG. 4 is a view for describing a problem in a case where the ultrasound transceiver 2101 is arranged on the distal portion side of the catheter and the optical transceiver 2102 is arranged on the drive shaft 2104 side. A corner 401 in FIG. 4 may become an obstacle of the light emitted from the optical transceiver 2102. However, in a case where the optical transceiver 2102 is moved to the ultrasound transceiver 2101 side, a distance from the electrode 2112 becomes shorter. Consequently, it is not preferable in that not only the optical transceiver 2102 is easily affected by the soldering, but also the soldering itself is less likely to be performed.

In addition, it is also conceivable to obliquely cut the corner 401. However, since a diameter of the drive shaft 2104 can be as small as approximately 0.5 mm, it may be difficult to carry out processing work for the corner 401. In addition, since the signal line 2105 extends to the space of the cutout portion, it can be difficult to effectively utilize the space due to the influence of wiring. According to the arrangement in the present embodiment illustrated in FIGS. 2 and 3, these problems can be solved.

Figure 5A:
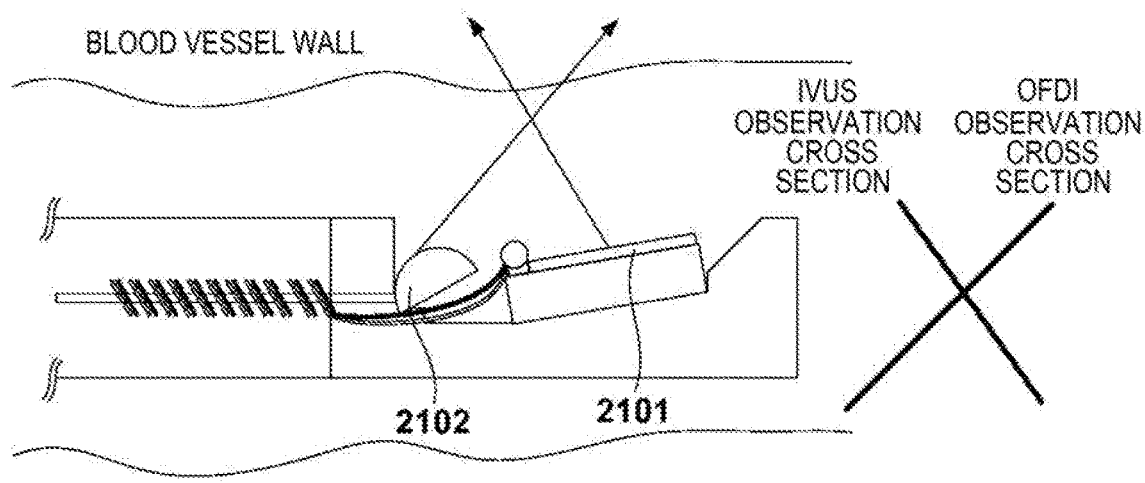
FIGS. 5A and 5B are views for describing an emitting direction (crossing or parallel) according to an embodiment of the present disclosure.
Figure 5B:
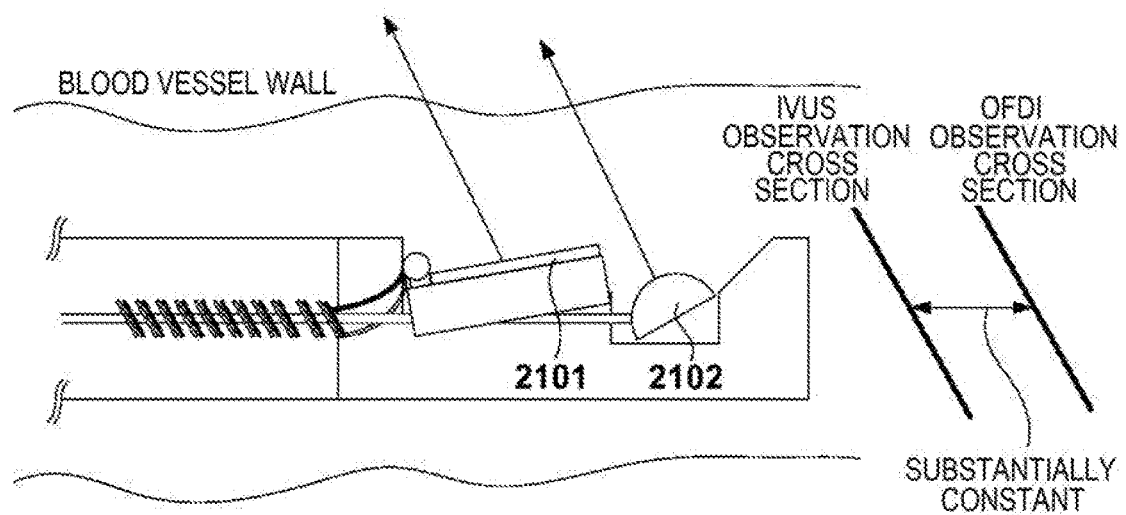

FIGS. 5A and 5B are views for describing a relationship between an emitting direction of the ultrasound wave from the ultrasound transceiver 2101 and an emitting direction of the light from the optical transceiver 2102. FIG. 5A illustrates a case where the respective emitting directions cross each other according to a configuration example in the related art illustrated in FIG. 4. FIG. 5B illustrates a case where the respective emitting directions are parallel to each other according to a configuration example in the embodiment of the present disclosure in FIG. 2. Even in a case where the emitting directions cross each other as illustrated in FIG. 5A, an IVUS observation cross-sectional image and an OCT observation cross-sectional image can be acquired. However, the emitting direction of the ultrasound wave and the emitting direction of the light are different from each other. Accordingly, it can be difficult to acquire the IVUS observation cross-sectional image and the OCT observation cross-sectional image for substantially the same cross section.

In contrast, if the emitting directions are substantially parallel to each other as illustrated in FIG. 5B, a substantially parallel image at regular intervals can be acquired. Based on a rotation speed of the drive shaft 2104, a pullback speed, and a beam emitting interval, respective frames are shifted from one another. In this manner, the IVUS observation cross-sectional image and the OCT observation cross-sectional image for substantially the same cross section can be acquired. Therefore, improved accuracy of intravascular diagnosis can be expected.

Figure 6A:
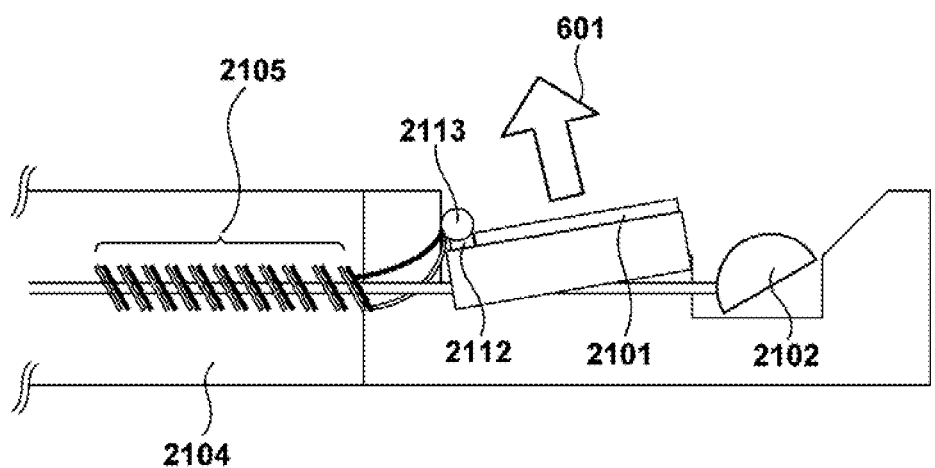
FIGS. 6A and 6B are views for describing an emitting direction (forward or rearward) according to an embodiment of the present disclosure.
Figure 6B:
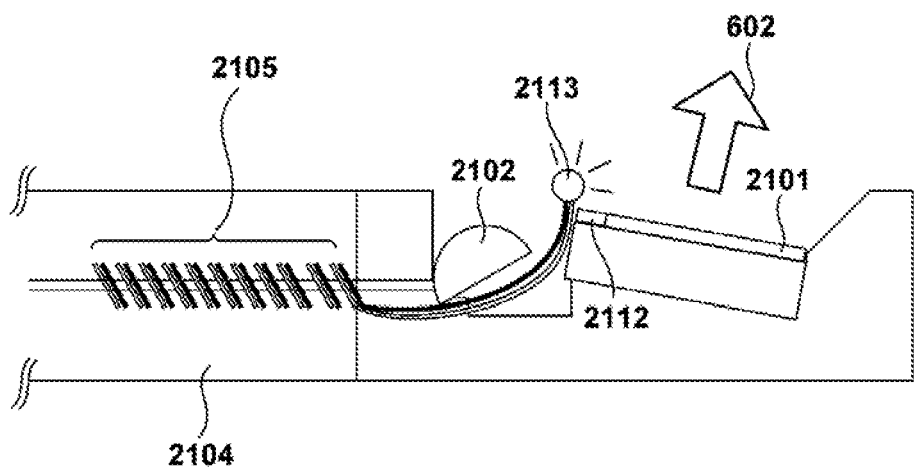

Furthermore, FIGS. 6A and 6B are views for describing a case where the electrode 2112 is affected by the emitting direction of the light from the ultrasound transceiver 2101. FIG. 6A illustrates a case of rearward emitting (arrow 601) according to a configuration example in the embodiment of the present disclosure in FIG. 2, and FIG. 6B illustrates a case of forward emitting (arrow 602) according to a configuration example in the related art illustrated in FIG. 4. Here, the rearward emitting means emitting in which the emitting direction of the light from the ultrasound transceiver 2101 is a direction tilting to the drive shaft 2104 side from a direction orthogonal to the drive shaft 2104. In addition, the forward emitting means emitting in which the emitting direction of the light from the ultrasound transceiver 2101 is a direction tilting to the catheter distal portion side from the direction orthogonal to the drive shaft 2104.

If the light is emitted forward, the emitting of the light from the ultrasound transceiver 2101 for IVUS increases exposed wiring of the signal line 2105 to the cutout portion space. Accordingly, the exposed wiring can be reduced by emitting the light rearward. In this manner, it is possible to effectively utilize an empty space. In addition, if the light is emitted forward, a load is likely to be applied to the electrode 2112, and joining strength of the soldering is weakened. The sensor is likely to be damaged after being detached from the solder 2113. From this point of view, the rearward emitting is suitable.

Note that in a case where the light and the ultrasound wave are emitted in the direction orthogonal to the drive shaft 2104, mainly the intensity of the reflected wave and the reflected light from the catheter sheath 230 is strong, thereby affecting a tomographic image to be acquired. Accordingly, as in the forward emitting or the rearward emitting, it can be desirable to emit the light and the ultrasound wave in a direction shifted from the vertical direction. Note that in FIGS. 6A and 6B, description has been made on the assumption of the configuration example in FIG. 4. However, even in the configuration example in FIGS. 2 and 3, the exposed wiring of the signal line 2105 to the cutout portion space decreases. If the light and the ultrasound wave are emitted forward, the load is still likely to be applied to the electrode 2112. Therefore, it can be desirable to similarly emit the light and the ultrasound wave rearward.

As described above, the imaging probe for diagnosis 101 according to the present embodiment can include the imaging core 210 having the drive shaft 2104 internally provided with the optical fiber 2106 and the signal line 2105. The imaging probe for diagnosis 101 can include the optical transceiver 2102 that is disposed in one end of the optical fiber 2106, and the ultrasound transceiver 2101 that is joined to the signal line 2105. The optical transceiver 2102 is arranged on the distal side of the imaging core 210 from the ultrasound transceiver 2101. The emitting direction of the ultrasound wave emitted from the ultrasound transceiver 2101 and the emitting direction of the light emitted from the optical transceiver 2102 are substantially parallel to each other, and are directions (rearward emitting) which further tilt to the proximal side (side where the drive shaft 2104 is present) of the drive shaft 2104 than the direction orthogonal to the drive shaft 2104.

In this way, an arrangement relationship between the ultrasound transceiver 2101 and the optical transceiver 2102 is configured as in the example illustrated in FIGS. 2 and 3. Accordingly, it is possible to minimize possibilities that lens performance may be affected by the scattered joining material during manufacturing of the imaging core 210 or the heat generated during joining. Furthermore, the light and the ultrasound wave are emitted rearward as illustrated in FIG. 5B. In this manner, it is possible to effectively utilize the space and to improve the joining strength.

The detailed description above describes an imaging probe for diagnosis used for diagnosing a biological lumen such as blood vessels. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging probe for diagnosis which includes an imaging core having a drive shaft internally provided with an optical fiber and a signal line, comprising:
   an optical transceiver that is disposed in one end of the optical fiber;
   an ultrasound transceiver that is joined to the signal line, and wherein the optical transceiver is arranged on a distal side of the imaging core from the ultrasound transceiver;
   an emitting direction of an ultrasound wave emitted from the ultrasound transceiver and an emitting direction of light emitted from the optical transceiver are parallel to each other, and wherein the emitting direction of the ultrasound wave emitted from the ultrasound transceiver and the emitting direction of the light emitted from the optical transceiver are directions which are further tilt to a proximal side of the drive shaft than a direction orthogonal to the drive shaft;
   a backing member being tabular and provided on a rear surface of the ultrasound transceiver;
   a groove disposed on a rear surface of the backing member and at a position separated from the ultrasound transceiver; and
   wherein the optical fiber extends through the groove.

2. The imaging probe for diagnosis according to claim 1, wherein a central axis of the optical fiber is eccentric from a central axis of the drive shaft.

3. The imaging probe for diagnosis according to claim 1, wherein the signal line and the ultrasound transceiver are joined to each other in one end on a side far from the optical transceiver, which is one end of the ultrasound transceiver.

4. The imaging probe for diagnosis according to claim 1, wherein the imaging core is further provided with a housing which is disposed in one end of the drive shaft and which has a cutout portion, and
   wherein the optical transceiver and the ultrasound transceiver are installed in the housing.

5. The imaging probe for diagnosis according to claim 1, wherein the signal line and the ultrasound transceiver are joined to each other by soldering.

6. An imaging probe for diagnosis, the imaging probe for diagnosis comprising:
   an imaging core having a drive shaft internally provided with an optical fiber and a signal line;
   an optical transceiver that is disposed in one end of the optical fiber;
   an ultrasound transceiver that is joined to the signal line;
   wherein the optical transceiver is arranged on a distal side of the imaging core from the ultrasound transceiver;
   a backing member being tabular and provided on a rear surface of the ultrasound transceiver;
   a groove disposed on a rear surface of the backing member and at a position separated from the ultrasound transceiver; and
   wherein the optical fiber extends through the groove.

7. The imaging probe for diagnosis according to claim 6, wherein a central axis of the optical fiber is eccentric from a central axis of the drive shaft.

8. The imaging probe for diagnosis according to claim 6, wherein the signal line and the ultrasound transceiver are joined to each other in one end on a side far from the optical transceiver, which is one end of the ultrasound transceiver.

9. The imaging probe for diagnosis according to claim 6, wherein the imaging core is further provided with a housing which is disposed in one end of the drive shaft and which has a cutout portion, and
   wherein the optical transceiver and the ultrasound transceiver are installed in the housing.

10. The imaging probe for diagnosis according to claim 6, wherein the signal line and the ultrasound transceiver are joined to each other by soldering.

11. The imaging probe for diagnosis according to claim 10, wherein an emitting direction of an ultrasound wave emitted from the ultrasound transceiver and an emitting direction of light emitted from the optical transceiver are parallel to each other, and wherein the emitting direction of the ultrasound wave emitted from the ultrasound transceiver and the emitting direction of the light emitted from the optical transceiver are directions which are further tilt to a proximal side of the drive shaft than a direction orthogonal to the drive shaft.

12. A diagnostic imaging probe, comprising:
   an imaging core having a drive shaft internally provided with an optical fiber and a signal line;
   an optical transceiver that is disposed in one end of the optical fiber;
   an ultrasound transceiver that is joined to the signal line, and wherein the optical transceiver is arranged on a distal side of the imaging core from the ultrasound transceiver;
   an emitting direction of an ultrasound wave emitted from the ultrasound transceiver and an emitting direction of light emitted from the optical transceiver are parallel to each other, and wherein the emitting direction of the ultrasound wave emitted from the ultrasound transceiver and the emitting direction of the light emitted from the optical transceiver are directions which are further tilt to a proximal side of the drive shaft than a direction orthogonal to the drive shaft;

a backing member having a rectangular shape with a rectangular cross section, and wherein the backing member is arranged on a bottom surface of the ultrasound transceiver;

a groove disposed on a rear surface of the backing member and at a position separated from the ultrasound transceiver; and wherein the optical fiber extends through the groove.

13. The diagnostic imaging probe according to claim 12, wherein a central axis of the optical fiber is eccentric from a central axis of the drive shaft.

14. The diagnostic imaging probe according to claim 12, wherein the signal line and the ultrasound transceiver are joined to each other in one end on a side far from the optical transceiver, which is one end of the ultrasound transceiver.

15. The diagnostic imaging probe according to claim 12, wherein the imaging core includes a housing in one end of the drive shaft and which has a cutout portion, and wherein the optical transceiver and the ultrasound transceiver are installed in the housing.

16. The diagnostic imaging probe according to claim 12, wherein the signal line and the ultrasound transceiver are soldered to each other.

\* \* \* \* \*